United States Patent [19]
Cronin et al.

[11] Patent Number: 5,166,191
[45] Date of Patent: Nov. 24, 1992

[54] USE OF RELAXIN IN CARDIOVASCULAR THERAPY

[75] Inventors: Michael Cronin, San Mateo; Phyllis L. Osheroff, Woodside; David G. Ward, Oakdale, all of Calif.

[73] Assignee: Genentech, Inc., South San Francisco, Calif.

[21] Appl. No.: 747,080

[22] Filed: Aug. 19, 1991

[51] Int. Cl.⁵ .................. A61K 37/02; C07K 7/40
[52] U.S. Cl. ...................................... 514/12; 530/324
[58] Field of Search ....................... 514/12; 530/324

[56] References Cited

U.S. PATENT DOCUMENTS

| | | |
|---|---|---|
| 4,656,249 | 4/1987 | Tregear . |
| 4,758,516 | 7/1988 | Hudson et al. . |
| 4,835,251 | 5/1989 | Burnier . |
| 4,871,670 | 10/1989 | Hudson et al. . |
| 5,023,321 | 6/1991 | Hudson et al. . |

FOREIGN PATENT DOCUMENTS

| | | |
|---|---|---|
| 251615 | 6/1987 | European Pat. Off. . |
| WO89/07945 | 2/1989 | PCT Int'l Appl. . |
| WO90/13659 | 4/1990 | PCT Int'l Appl. . |

OTHER PUBLICATIONS

Sherwood, O. D., *The Physiology of Reproduction*, Chapter 16 "Relaxin", Knobil, E. and Neill, J. et al. (eds.) Raven Press, Ltd. New York, 1988, pp. 585-673.
Isaacs et al., *Nature* 271, 278 (1978).
Weiss et al., *Chem. Abstr.* 88, 224 88:71076g (1978).
Bigazzi et al., *Chem. Abstr.* 95, 366 95:12753x (1981).
Hudson et al., *Nature* 301, 628 (1983).
Hudson et al., *EMBO J.* 3, 2333 (1984).
Tregear et al., *Relaxin*, Bryant-Greenwood, Niall and Greenwood (eds.), Elsevier, 1981, pp. 152-164.
Johnston et al., in *Peptides: Structure and Function*, Proc. Ninth Am. Peptide Symp., Deber, C. M. et al. (eds.), Pierce Chem. Co. 1985.
Tregear et al., in *Biology of Relaxin and its Role in the Human*, Bigazzi et al. (eds.) Elsevier N.Y., N.Y. 42-55.

O'Byrne et al., *J. Clin. Endocr. and Metabol.* 47, 1106 (1978).
Sherwood et al., *Endocrinology* 107, 691 (1980).
Bell et al., *Obstet. Gynecol.* 69, 585 (1987).
Stewart et al., *J. Clin. Endo. Metab.* 70, 1771 (1990).
Aoi et al., *Proc. Soc. for Exp. Biol. and Med.* 153, 13 (1976).
Chesley, C. C., *Hypertensive Disorders in Pregnancy*, Appleton Century-Crofts publ. 119-153 (1978).
Moutquin et al., *J. Gyn. Obst. Biol. Rep.*, 11, 833 (1982).
Clapp, J. F., *Am. J. Obstet. Gynecol.* 152, 659 (1985).
Massicotte et al., *Clin. and Exp. Hyper.-Hyper. in Pregnancy* B5(2), 135 (1986).
Robson et al., *Am. J. Physiol.* 256, H1060 (1989).
Miller et al., *J. Pharmacol. Exp. Ther.* 120, 426 (1957).
Braddon, S. A., *Endocrinology* 102, 1291 (1978).
Porter et al., *J. Endocr.* 83, 18 (1979).
Sanborn et al., *Endocrinology* 106, 1210 (1980).
Judson et al., *J. Endocr.* 87, 153 (1980).
Nishikoro et al., *Endocrinology* 111, 1743 (1982).
Nishikori et al., *J. Biol. Chem.* 258, 2468 (1983).
Del Mese et al., in "Biology of Relaxin and its Role in the Human", Bigazzi et al. (eds.), 291-293 (1983).
St-Louis, J. and Massicotte, G., *Life Sciences* 37, 1351 (1985).
O'Byrne et al., *J. Physiol.* 561, 49P (1985).
Bigazzi et al., *Acta Endocrinol.* 112, 296 (1986).
Jones, S. A. and Summerlee, A. J. S., *J. Physiol.* 381, 37P (1986).
O'Byrne et al., *J. Endocr.* 109, 393 (1986).
Cronin et al., *Biochem. Biophys. Res. Comm.* 148, 1246 (1987).

(List continued on next page.)

*Primary Examiner*—Howard E. Schain
*Assistant Examiner*—Choon Koh
*Attorney, Agent, or Firm*—Ginger R. Dreger

[57] ABSTRACT

The invention concerns the use of relaxin in the cardiovascular therapy, and specifically in the treatment of acute and chronic heart failure.

23 Claims, 10 Drawing Sheets

OTHER PUBLICATIONS

Jones, S. A. and Summerlee, A. J. S., *J. Endocr.* 114, 241 (1987).
Dayanithi et al., *Nature* 325, 813 (1987).
Massicotte et al., *P.S.E.M.B.* 190, 254 (1988).
Chen et al., *Biol. Reprod.* 39, 519 (1988).
Mumford et al., *J. Endocrinol.* 122, 747 (1989).
Ahokas et al., *Am. J. Obstet. Gynecol.* 161, 618 (1989).
Parry et al., *J. Neuroendocrinol.* 2, 53 (1990).
Parry et al., *Endocrinol.* 129, 47 (1991).
Kramer et al., *In Vitro Cell. Dev. Biol.* 26, 647 (1990).
Ward et al., *Am. J. Physiol.* 261, H206 (1991).
Casten et al., *Angiology XI,* 408 (1960).
Casten et al., *J.A.M.A.* 166, 319 (1958).
Ward et al., Genentech Reports No. 88-485-350-561 (1989).
Mercado-Simmen et al., *J. Biol. Chem.* 255, 3617 (1980).
Mercado-Simmen et al., *Biology of Reproduction* 26, 120 (1982).
Mercado-Simmen et al., *Endocrin.* 110, 220 (1982).
Osheroff, P. L., *J. Biol. Chem.* 265, 9396 (1990).
Osheroff, P. L. and Phillips, H. S., *Proc. Natl. Acad. Sci.* 88, 6413 (1991).
Schramm et al., *Arzneim-Forsch.* 33, 1268 (1983).
Evans et al., *Pharmacologist* 25, 550 (1983).
Evans et al., *Drug Develop. Res.* 9, 143 (1986).
Taylor et al., *Ann. Rep. in Med. Chem.* 22, 85 (1987).
Weishaar et al., *Cardiovasc. Drugs and Ther.* 3, 29 (1989).
Steffen et al., *J. Cardiovasc. Res.* 9,143 (1986).
Steffen et al., *New Cardiovascular Drugs,* Raven Press, New York, p. 81 (1986).

FIG.IA
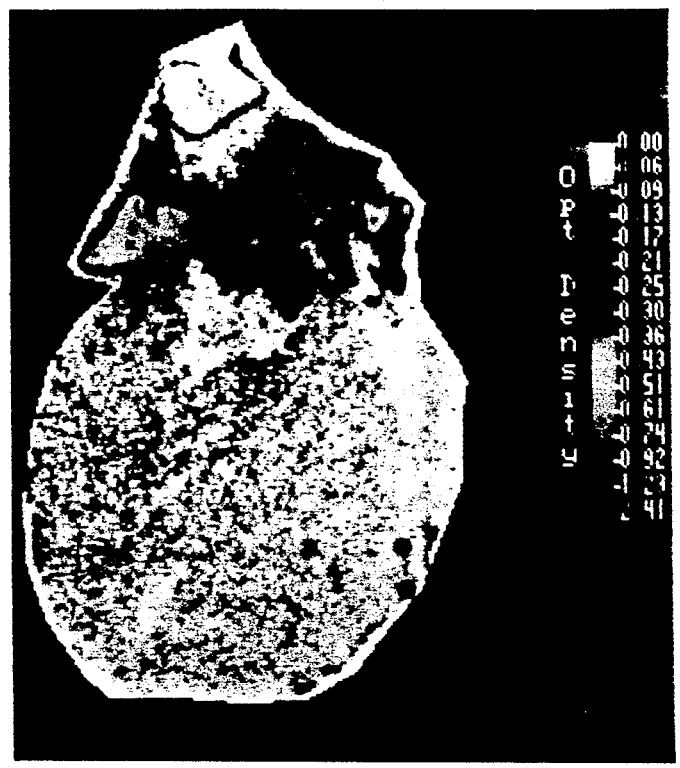
FIG.IC
FIG.IB
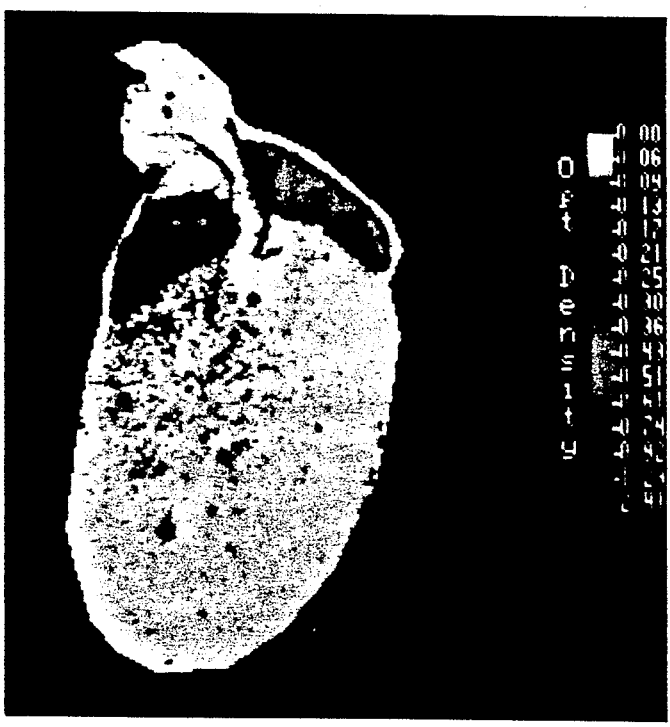
FIG.ID

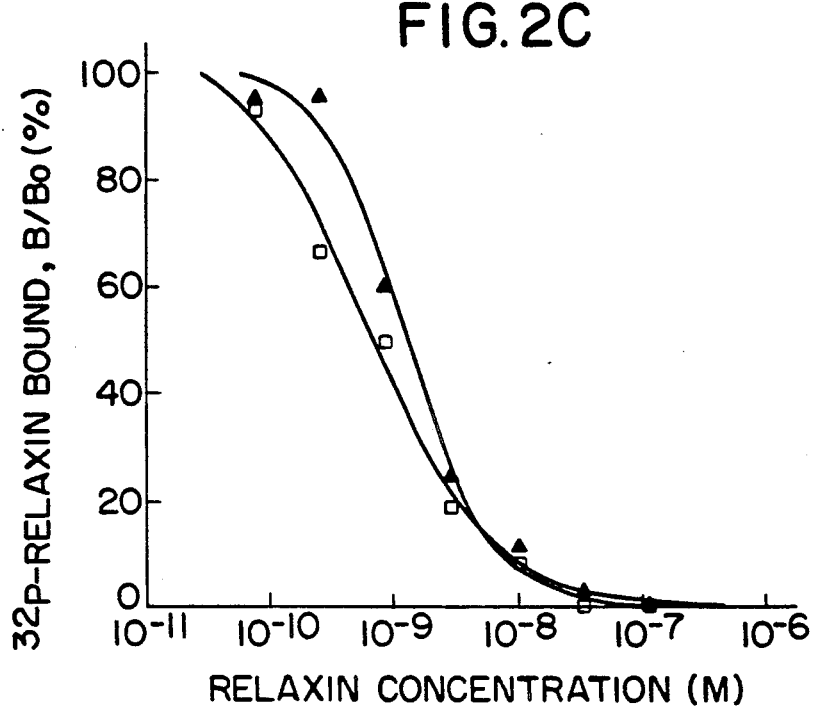
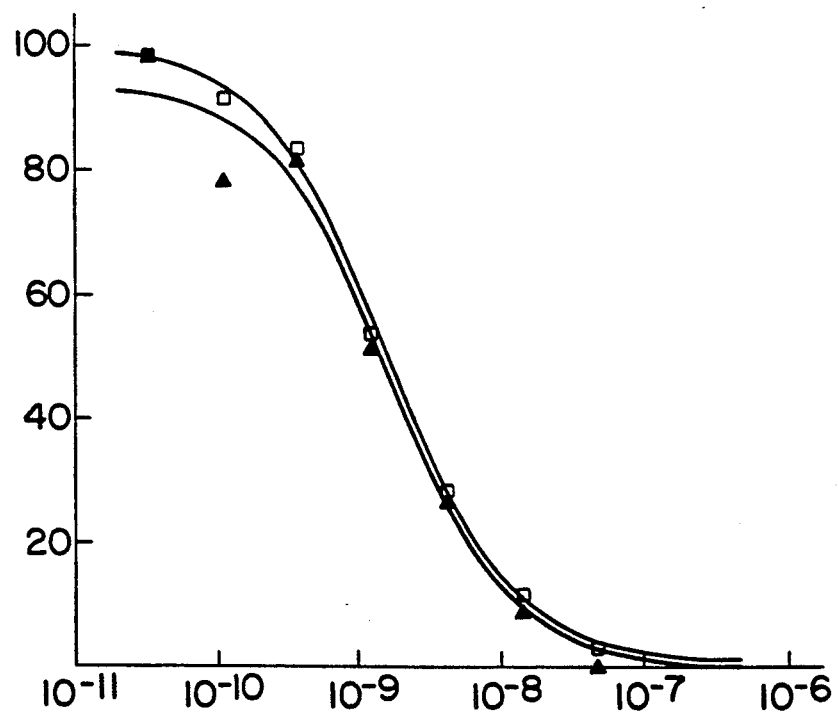

USE OF RELAXIN IN CARDIOVASCULAR THERAPY

FIELD OF THE INVENTION

This invention is from the field of cardiovascular therapy. More particularly, this invention concerns the use of relaxin in cardiovascular therapy, and specifically in the treatment of heart failure.

BACKGROUND ART

Heart failure is defined as the inability of the cardiac pump to move blood as needed to provide for the metabolic needs of body tissue. Decreases in pumping ability arise most often from loss or damage of myocardial tissue. As a result, ventricular emptying is suppressed which leads to an increase in ventricular filling pressure and ventricular wall stress, and to a decrease in cardiac output. As a physiological response to the decrease in cardiac output, numerous neuroendocrine reflexes are activated which cause systemic vasoconstriction, sympathetic stimulation of the heart and fluid retention. Although these reflex responses tend to enhance cardiac output initially, they are detrimental in the long term. The resulting increases in peripheral resistance increase the afterload on the heart and the increases in blood volume further increase ventricular filling pressure. These changes, together with the increased sympathetic stimulation of the heart, lead to further and often decompensating demands on the remaining functional myocardium.

Congestive heart failure, which is a common end point for many cardiovascular disorders, results when the heart is unable to adequately perfuse the peripheral tissues. According to recent estimates, there are about 4 million people in the United States diagnosed with this disease, and more than 50% of these cases are fatal within 5 years of diagnosis [Taylor, M. D. et al., Annual Reports in Med. Chem. 22, 85-94 (1987)].

Current therapy for heart failure, including congestive heart failure, focuses on increasing cardiac output without causing undue demands on the myocardium. To achieve these ends, various combinations of diuretics, vasodilators and inotropic agents are used to decrease blood volume, to decrease peripheral resistance, and to increase force of cardiac contraction. Current therapy therefore depends on balancing the effects of multiple drugs to achieve the clinical needs of individual patients, and is plagued by adverse reactions to the drugs used.

For example, diuretics decrease plasma concentrations of potassium and magnesium and increase the incidence of arrhythmias in patients receiving digitalis. Diuretics can potentiate the circulatory effects of nitrates through volume depletion and lead to decreases in filling pressure of the heart, cardiac output and systemic arterial pressure.

Alpha adrenergic antagonists can lead to marked falls in systemic arterial pressure that compromise coronary perfusion.

Angiotensin converting enzyme inhibitors can have similar effects on arterial pressure and additionally lead to excessive increases in plasma concentrations of potassium.

Drugs that lead to positive inotropy, such as digitalis and beta adrenergic antagonists, have the potential to provoke arrhythmias. In addition, digitalis has a narrow therapeutic index and the catecholamine analogs all tend to loose their effectiveness rapidly, due to receptor downregulation.

Thus there is a need for therapeutic agents that lead to physiologically integrated responses of arterial and venous vasodilation and cardiac inotropy, and are devoid of the disadvantages of the currently used therapeutic agents.

Mature human relaxin is a disulfide bridged polypeptide hormone of approximately 6000 daltons, which is known to show a marked increase in concentration during pregnancy in many species, and is known to be responsible for remodelling the reproductive tract before parturition, thus facilitating the birth process.

Relaxin was discovered by F. L. Hisaw [Proc. Soc. Exo. Biol. Med. 23, 661 (1962)] and received its name from Fevold et al. [J. Am. Chem. Soc. 52, 3340 (1930)] who obtained a crude aqueous extract of this hormone from sow corpora lutea. A multitude of observations with crude relaxin preparations led to the view that relaxin probably plays an important role during pregnancy and parturition.

Between 1974 and 1981, highly purified relaxin was isolated from the ovaries of pregnant pigs [Sherwood and O'Byrne Arch. Biochem. Biophys. 160, 185 (1974)], rats [Sherwood, O. D., Endocrinology 104, 886 (1979)], and sharks [Reinig et al., Endocrinology 109, 537 (1981)]. More recently, highly purified relaxin was isolated from the placentas of horses [Stewart, D. R. and Papkoff, Endocrinology 119, 1093 (1986)] and rabbits [Eldridge, R. K. and Fields, P. A., in Biology of Relaxin and its Role in the Human M. Bigazzi et al., eds. 389-391, Excerpta Medica, Amsterdam (1983)]. Partially purified relaxin was obtained from cow and human corpora lutea (CL), placentas, and decidua. In the human, relaxin is known to exist in most abundance in the corpora lutea of pregnancy, however, relaxin has also been detected in nonpregnant female as well as in the male (seminal fluid) [Bryant-Greenwood, G. D., Endocrine Reviews 3, 62-90 (1982) and Weisse, G., Ann. Rev. Physiol. 46, 43-52 (1984)].

The availability of purified relaxin has enabled the amino acid sequence determination of relaxin from pig [James et al., Nature 267, 544 (1977); Schwabe et al., Biophys. Res. Commun. 75, 503 (1977)], rat [John et al., Endocrinology 108, 726 (1981)] and shark [Schwabe et al., Ann. N.Y. Acad. Sci. 380, 6 (1982)].

Efforts have been made to purify relaxin from human corpora lutea, placentas and decidua but none of the human relaxin preparations were demonstrated to be highly purified.

Recombinant techniques have first been applied to the isolation of cDNA clones for rat and porcine relaxins [Hudson et al., Nature 291, 127 (1981); Haley et al., DNA 1, 155 (1982)]. Two human gene forms have been identified by genomic cloning using probes from the porcine relaxin gene [Hudson et al., Nature 301, 628 (1983); Hudson et al., EMBO J. 3, 2333 (1984); and U.S. Pat. Nos. 4,758,516 (issued Jul. 19, 1988) and 4,871,670 (issued Oct. 3, 1989)], although only one of these gene forms (termed H2) has been found to be transcribed in corpora lutea. It is unclear whether the other gene is expressed at another tissue site, or whether it represents a pseudo-gene. The fact that H2 relaxin is synthesized and expressed in the ovary suggests that this is the sequence that is directly involved in the physiology of pregnancy.

Relaxin consists of two peptide chains, referred to as A and B, joined by disulfide bonds with an intra-chain disulfide loop in the A-chain in a manner analogous to that of insulin. The two human relaxin genes show considerable nucleotide and amino acid sequence homology to each other, however, there are some notable regions of sequence divergence, particularly in the amino-terminal region of both A- and B-chains.

The structure of relaxin has apparently diverged considerably among species during evolution. Only 40% to 48% amino acid sequence homology exists among porcine, rat, shark, and human relaxins.

Similar to all species examined, the primary translation product of H2 relaxin is a preprorelaxin consisting of a 25 amino acid signal sequence followed by a B chain of about 29-33 amino acids, a connecting peptide of 104-107 amino acids (C peptide), and an A chain of 24 amino acids. During the biosynthesis of relaxin, the signal peptide is removed rapidly as the nascent peptide chain is translocated across the endoplasmic reticulum. The further processing of the prohormone obtained into relaxin, and especially the function of the C peptide in relaxin is not entirely understood. One function presumably is to direct the folding of the precursors so that the correct disulfide bonds are formed between the B and A chains.

A concise review of the knowledge about relaxin as of 1988 was provided by Sherwood, D. in *The Physiology of Reproduction* Chapter 16, "Relaxin", Knobil, E. and Neill, J. et al., (eds.) Raven Press, Ltd., New York pp. 585-673 (1988).

It is known that relaxin increases in peripheral plasma 7-10 days after the midcycle surge of luteinizing hormone and continues to rise if conception has occured, obtaining levels of over 800 pg/ml by three weeks [Stewart, D. R. et al., *J. Clin. Endo. Metab.* 70, 1771-1773 (1990)]. During pregnancy, serum concentrations of relaxin, as measured by a homologous radioimmunoassay, is highest by about the 10th week, obtaining levels of about 500 pg/ml for the remainder of pregnancy [Bell, R. J. et al., *Obstet. Gynecol.* 69, 585-589 (1987)].

In view of the above and similar physiological findings, relaxin has been consistently associated with the condition of pregnancy, and most of its known utilities are associated with this condition.

H2 relaxin has been described to remodel the reproductive tract to facilitate birth process, including ripening of the cervix, thickening of the endometrium of the pregnant uterus as well as increased vascularization to this area, and an effect on collagen synthesis. H2 relaxin has also been associated with lactation, and some reports indicate that relaxin has a growth-promoting effect on mammary tissue [Wright, L. C. and Anderson, R. R., *Adv. Exp. Med. Biol.* 143, 341 (1982)].

It has been observed that Raynaud's lesions completely disappear during early pregnancy. Clinical studies, which derived from this observation, have shown that an ovarian derived porcine relaxin was beneficial in healing Raynaud's lesions arising from obliterative peripheral arterial disease [Casten, G. C. and Boucek, R. J., *J. Am. Med. Assoc.* 166, 319-324 (1958); Casten, G. C., et al., *Angiology* 11, 404-414 (1960)].

There are indications that relaxin might be present in the male reproductive tract. Human seminal plasma was reported to contain relaxin bioactivity [Weiss et al., *Am. J. Obstet. Gynecol.* 154, 749 (1986)], and relaxin is believed to enhance the mobility of human spermatozoa.

Given the effect of relaxin on the connective tissue, it has been suggested that relaxin may improve skin elasticity.

It has been observed that in pregnant women heart rate increases by 2 weeks after conception, showing an elevation of about 7 beats/min, and continues to rise, obtaining elevations of about 10 beats/min by the 10th week [Clapp, J. F., *Am. J. Obstet. Gynecol.* 152, 659-660 (1985)]. This change in early pregnancy is coincident with the first elevation of circulating relaxin in pregnant women [Stewart, D. R. et al., Supra].

Similarly, cardiac output increases and total peripheral resistance decreases by three weeks after conception, showing changes of $+0.52$ liter/min and $-113$ $dyn.s^{-1}.cm^{-1}$, respectively. Cardiac output continues to increase and total peripheral resistance continues to decrease, reaching $+2.21$ l/min and $-433$ $dyn.s^{-1}.cm^{-5}$, respectively at between 10 and 14 weeks before leveling off near these values [Robson, S. C. et al., *Am. J. Physiol.* 256, H160-H1065 (1989)].

There are sporadic reports on the effect of relaxin administration on blood vessels, and blood pressure under special circumstances, without any written indication that the reported observations could have any potential therapeutic implications.

Local application of porcine relaxin to the rat mesocaecum was found to dilate venules and antagonized the vasoconstrictive effects of norepinephrine and pormethazine [Bigazzi, M. et al., *Acta Endocrinol.* 112, 296-299 (1986); DelMese, A. et al., in *Biology of Relaxin and its Role in the Human*, Bigazzi, M. et al. (eds.) 291-293, Excerpta Medica, Amsterdam (1983)]. Chronic infusion of rat relaxin for two days to spontaneously hypertensive rats has reportedly led to blunted vasoconstrictive effects of norepinephrine and vasopressin on perfused mesenteric artery [Massicotte et al., *Proc. Soc. Exp. Biol. Med.* 190, 254-259 (1989)]. However, the physiological significance of these observations remains obscure, and it is not known whether or not relaxin affects total peripheral resistance.

Even more confusing and contradictory are some reports on the possible effects of relaxin on arterial blood pressure.

Miller et al. [*J. Pharmacol. Exp. Ther.* 120, 426-427 (1957)] first reported that injection of an extract of pregnant sow ovary caused a transient fall in blood pressure when injected into anesthetized dogs. In contrast, injection of an extract of up to 50 $\mu$g purified porcine relaxin in anesthetized rats did not affect blood pressure [Porter et al., *J. Endocrinol.* 83, 183-192 (1979)].

Chronic infusion of rat relaxin has been reported to have no effect on arterial pressure in normotensive non-pregnant rats [St. Louis, J. and Massicotte, G., *Life Sci.* 37. 1351-1357 (1985)] or in pregnant rats [Ward, D. G., *Am. J. Physiol.* 261: in press (1991)].

Other publications indicate that intravenous injection of porcine relaxin in urethane anesthetized rats increases arterial pressure [Jones, S. A. and Summerlee, A. J. S., *J. Physiol.* (London), 381:37P (1986); Mumford, A. D. et al., *J. Endocrinology* 122, 747-755 (1989); Parry et al., *J. Neuroendocrinology* 2, 53-58 (1990)]. The increase in parterial pressure is thought to be mediated predominantly by the release of vasopressin [Parry, L. J. et al., *J. Neuroendocrinology* 2, 53-58 (1990)].

Intracerebroventricular injection of porcine relaxin was found to increase arterial pressure in the urethane anesthetized rat [Mumford, A. D., et al., *J. Endocrinology* 747-755 (1989)].

In view of these contradictory findings, the effect of relaxin on arterial pressure is at best unclear.

Intravenous or intracerebroventicular injection of porcine relaxin has been found to increase heart rate in the urethane anesthetized rat [Parry, L. J. et al., *J. Neuroendocrinology* 2, 53-58 (1990); Mumford, A. D. et al., *J. Endocrinology* 122, 747-755 (1989)].

The interpretation of the various physiological effects of relaxin is very difficult, as little is known about the mechanism of action of relaxin at the molecular level. Relaxin is known to increase cAMP levels in uterine tissues or cells [Braddon, S. A. *Endocrinology* 1292-1299 (1978); Sanborn, B. M. et al., *Endocrinology* 106, 1210-1215 (198)); Judson, D. G. et al., *J. Endocrinology* 87, 153-159 (1980); Chen, G. et al., *Biol. Reprod.* 39, 519-525; Kramer, S. M. et al., *In Vitro Cell. Dev. Biol.* 26 647-656 (1990)], and also in pituitary cells [Cronin, M. J. et al., *Biochem. Biophys. Res. Commun.* 148, 1246-1251 (1987)], but there is no conclusive evidence how cAMP acts as a mediator of relaxin actions.

Relaxin is reported to decrease uterine myosin light chain kinase activity and myosin light chain phosphorylation, which in turn inhibits the Ca.-activated actyomyosin ATPase in estrogen-primed rat uteri [Nishikori et al., *Endocrinology* 111, 1743-1745 (1982); Nishikori et al., *J. Biol Chem.* 258, 2468-2474 (1983)]. The mechanism by which relaxin inhibits the myosin light chain kinase has yet to be elucidated.

Another important area of research for the understanding of the mechanism of action of relaxin, namely the relaxin receptors, is also in an early stage. Previously, Mercado-Simmen et al. [*J. Biol. Chem.* 255, 3617-3623 (1980); *Endocrinology* 110, 220-226 (1982); *Biol. Reprod.* 26, 120-128 (1982)] reported the partial characterization of rat and porcine uterine and porcine cervical relaxin receptors using $^{125}$I-labeled porcine relaxin. The $^{125}$I-labeled porcine relaxin was only partially purified over a Sephadex column, and was not substantially characterized chemically. The availability of biologically active, synthetic human relaxin whose structure is based on the nucleotide sequence obtained from ovarian cDNA clones, has recently allowed the first study of specific human relaxin receptors [Osheroff, P. L., *J. Biol. Chem.* 265. 9396-9401 (1990)].

SUMMARY OF THE INVENTION

The present invention is based on the entirely unexpected finding that relaxin binds specifically and with high affinity to receptors in the cardiac atria of both male and female rats.

The present invention is further based on the unexpected finding that cardiac atria from rat hearts respond directly to relaxin, and more specifically that relaxin increases the rate of contraction in isolated and spontaneously beating right atrium and the force of contraction in isolated and electrically paced left atrium.

In view of the fact that relaxin is best known as a pregnancy-associated hormone, our finding of relaxin binding sites in the heart of both male and unpregnant female rats was unpredicted.

As cardiac atria from (male and female) rat hearts respond directly to relaxin with an increase in rate and force of contraction, relaxin is useful for the treatment of (chronic and acute) heart failure.

In one aspect, the present invention relates to a method for increasing cardiac output by administering to a patient exhibiting pathologically diminished cardiac output a therapeutically effective amount of a compound capable of specific binding to a relaxin receptor in the atrium of the heart and increasing the force or rate of atrial contraction.

In another aspect, the present invention relates to a method of treating heart failure by administering to a patient in need of such treatment a therapeutically effective amount of a compound capable of specific binding to a relaxin receptor in the atrium of the heart and increasing the force or rate of atrial contraction.

In a further aspect, the present invention concerns a method of stimulating cardiac inotropy and chronotropy, comprising administering to a patient in need of such stimulation a therapeutically effective amount of a compound capable of specific binding to a relaxin receptor in the atrium of the heart and increasing the force or rate of atrial contraction.

In a still further aspect, the present invention relates to a method of restoring cardiac function following acute heart failure comprising intravenously administering to a patient in need of such treatment a liquid pharmaceutical formulation comprising a compound capable of specific binding to a relaxin receptor in the atrium of the heart, in an amount capable of restoring myocardial contractility to a predepression level.

In a preferred embodiment of these methods relaxin, more preferably human relaxin (both as hereinafter defined) is used.

These and further aspects of the invention will be apparent from the detailed description that follows.

BRIEF DESCRIPTION OF DRAWINGS

FIG. 1 is a pseudocolor representation of the binding of $^{32}$P-H2 relaxin (further referred to as $^{32}$P relaxin) (100 pM) to female rat heart in the absence (A) and presence of 100 nM unlabeled relaxin (B), and 100 nM IGF-I (C). The binding of 100 pM $^{32}$P-relaxin to male rat heart is shown in FIG. 1D. Binding to tissue sections and computer-assisted image analysis of the binding autoradiographs were performed as described in Example 1. Low to high binding intensities are shown in OD units and represented by a color spectrum from magenta to red. The arrow in A points to the regions of atria. See FIG. 4E for histology.

FIG. 3 shows the displacement of the binding of $^{32}$P-H2 relaxin by unlabeled H1 relaxin in the atria of female rat heart. □ left atrium; right atrium.

DETAILED DESCRIPTION OF THE INVENTION

Figure 2A:
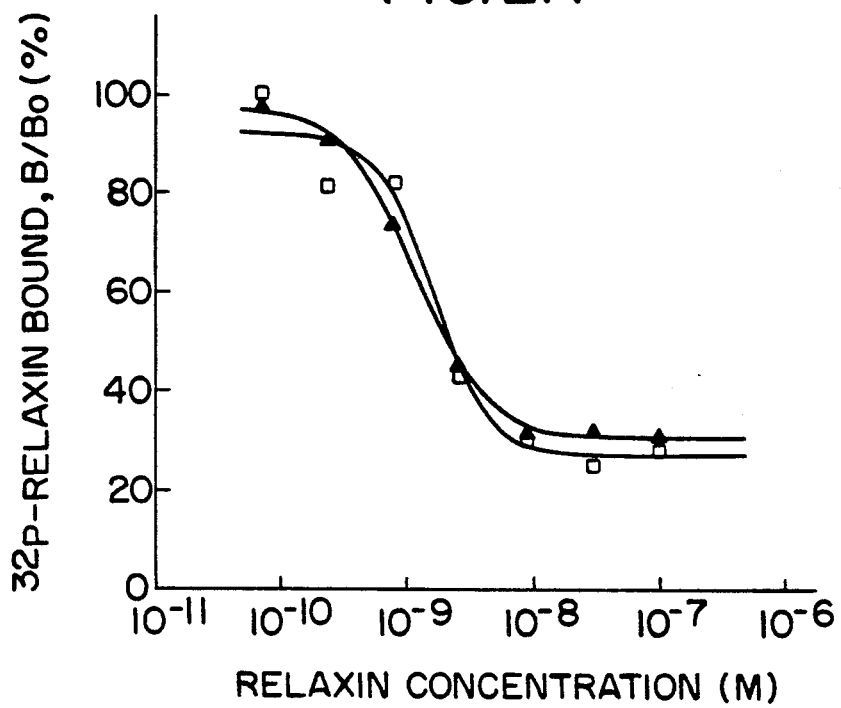
FIG. 2 shows the displacement of the binding of $^{32}$P-relaxin by unlabeled relaxin in the rat uterus (A), the atria of female rat heart (B), and the atria of estrogen-treated overiectomized rat (C). Consecutive tissue sections were incubated with 100M $^{32}$P-relaxin in the absence (Bo) and presense (B) of increasing concentrations of unlabeled relaxin. Binding intensities were analyzed by computerized densitometry and expressed as OD units or radioactivity (cpm). In detail, a square of uniform predetermined size (9 mm$^2$ on the RAS-3000 screen) was placed on the areas of maximum binding in each particular region. The OD or cpm represents the integrated intensity within that particular square, based on parallel $^{32}$P-relaxin standards ranging from 50-2000 cpm. Background binding was subtracted from all readings. Binding intensities corresponding to an OD of 0.05 were readily detected and resolved from background binding. Each point represents the mean of the five highest binding areas within each region. The two curves in each panel represent determinations on two separate regions on each tissue: in A. uterine horn, □ cervix; in B and C Δ, right atrium, □ left atrium. The displacement data were fit to a four-parameter equation and the dissociation constant ($K_d$) for relaxin was calculated to be 1.3±0.22 nM in A; 1.37±0.13 nM in B; and 0.86±0.35 nM in C.

Before the present invention, receptors for relaxin have been partially characterized in rat and porcine uterine and in porcine cervical membranes by using $^{125}$I-labeled porcine relaxin which was only partially purified and was not characterized chemically [Mercado-Simmen, R. C. et al., *J. Biol. Chem.* 255, 3617–3623 (1980); Mercado-Simmen, R. C., et al., *Endocrinology* 110, 220–226 (1982); Mercado-Simmen, R. C., et al., *Biol. Reprod.* 26, 120–128 (1982)]. Using a biologically active $^{32}$P-labeled human relaxin ($^{32}$P-relaxin), specific relaxin binding sites have recently been identified in rat uterus, cervix and brain by ligand autoradiography [Osheroff, P. L. et al., *J. Biol. Chem.* 265, 9396–9401 (1990); Osheroff, P. L. and Phillips, H. S., *Proc. Natl. Acad. Sci. USA*, 88, 6413–6417 (1991)].

The present invention is based on the localization of specific relaxin binding sites (receptors) in the atria of both female and male rat hearts.

The present invention is further based on the experimental finding that relaxin increases the rate of contraction in isolated and electrically paced left atria of rats. Because no differences were observed in receptor affinity for relaxin in cardiac atria between male and female rats, measurements were obtained in male rats. Both the rate of contraction and the force of contractions increased in a dose dependent manner.

These data show that the cardiac atria from rat hearts respond directly to relaxin with an increase in rate and force of contraction.

As relaxin is best known as a sex-dependent peptide hormone with an important role in the physiology of pregnancy, our results evidencing the presence of specific relaxin receptors in the heart of rats of both sexes, and the direct effect of relaxin on the cardiac atria from male and female rats are highly intriguing, and make relaxin a candidate for the treatment of acute and chronic heart failure, in particular congestive heart failure, and other cardiovascular disorders.

As used throughout the specification and claims, "relaxin" denotes a functional relaxin protein capable of increasing the force or rate of atrial contraction. Structurally, the term "relaxin" is meant to include polypeptides comprising the amino acid sequence of a naturally occurring (human or non-human animal, such as porcine, murine, etc.) relaxin, or comprising an amino acid sequence which differs from such native relaxin amino acid sequences by substitutions, deletions, additions and/or modifications of one or more amino acid residues in the A- and/or the B-chain of the respective native relaxin, as well as glycosylation variants, unglycosylated forms, organic and inorganic salts, covalently modified derivatives of such native and modified polypeptides, provided that the qualitative ability of increasing the force or rate of contraction of the atrial muscle is retained. "Relaxin" as defined herein generally has a sequence greater than about 70% homologous with the B- or A-chain of a native relaxin polypeptide. Preferably, the homology is greater than about 75%, more preferably about 80%. This definition specifically includes prepro-, pro- and mature human relaxin, including its H2 and H1 forms (see U.S. Pat. Nos. 4,758,516, issued Jul. 17, 1988 and 5,023,321, issued Jun. 11, 1991 for H2 relaxin; U.S. Pat. No. 4,871,670, issued Oct. 30, 1989 for H1 relaxin; and Sherwood, O. D., supra disclosing both human gene sequences along with non-human animal relaxin sequences). When synthetic H2 relaxin and certain human relaxin analogs were tested for biological activity, the tests revealed a relaxin core necessary for biological activity as well as certain amino acid substitutions for methionine that did not affect biological activity [Johnston et al., in *Peptides: Structure and Function*, Proc. Ninth American Peptide Symposium, Deber, C. M. et al. (eds.) (Pierce Chem. Co. 1985)]. Our finding that, despite the very limited amino acid sequence identity, all mammalian relaxins (including human H2 and H1 relaxins) so far isolated are biologically active in the rat also indicate the presence of a specific conserved region on the relaxin molecules from different species that interacts with the rat receptors [see also Kemp, B. E. and Niall, H. D., *Vitam. Horm.* (NY) 41, 79–115 (1984)]. Accordingly, this "core peptide" is specifically included within this definition.

. The term "human relaxin" is used in an analogous sense, including all human relaxin molecules, fragments and derivatives, as hereinabove defined. This definition specifically includes relaxin analogs having amino acids 1-24 to 10-24 of human H2 relaxin A-chain, and amino acids −1-32 to 10-22 of human H2 relaxin B-chain. Preferred are combinations of any one of A-chains A(1-24), A(2-24) and A(3-24) with any one of B-chains B(−1-23) to B(−1-32) (see U.S. Pat. No. 5,023,321).

The relaxin analogs preferably have a full-length A-chain and a carboxy-terminal shortened B-chain of either gene form. It has been found by mass spectroscopic ionization using fast-atom bombardment that the predominant species of human relaxin in the corpus luteum and serum is the H2 relaxin form with a full-length A-chain and with a B-chain in which the four C-terminal amino acids are absent so that the B-chain ends with a serine at position 29. This form [H2(B29A24), also referred to as "short relaxin" as opposed to the "long relaxin" containing a B chain of 33 amino acids] is particularly preferred. A typical substitution is the replacement of methionine in the native human relaxin sequence with different amino acids, e.g. lysine or alanine. Examples of such human relaxin analogs include, but are not limited to H1(B2-27 A 24) $_B$Ala$^{25}$; H2(B2-25 A24); H2(B33 A24); H2(B33 A24) $_B$Lys$^4$ $_B$Ala$^{25}$; H2(B2-33 A24) $_B$Lys$^4$ $_B$Ala$^{25}$; H2(B2-33 A24) $^4$pyro-Glu$^1$ $_B$Lys$^4$ $_B$Ala$^{25}$; and H2(B33 A24) $_A$pyro-Glu$^1$$_B$Lys$^4$ $_B$Ala$^{25}$. The nomenclature is as follows: H1, H2 refer to the two human genes which encode human relaxin. A and B refer to the respective chains of human relaxin. The numbers following A or B refer to the length of the chain, i.e. number of amino acids comprising the A- or B-chain. Amino acids are designated by their customary three letter notation. The subscript preceding the amino acid designates the A- or B-chain in which the amino acid is located while the superscript following the amino acid refers to the position in the chain.

The terms "naturally occurring (human) relaxin" and "native (human) relaxin" are used to collectively refer to mature full length relaxin molecules having the amino acid sequence as occurring in nature, either isolated from natural source, recombinantly produced or chemically synthesized, or produced by any combination of such methods. For human relaxin, these definitions cover the mature, full length H1 and H2 polypepites having the amino acid sequences disclosed in Hudson et al., *Nature*, Supra, and Hudson et al., *EMBO J.*, Supra. and in U.S. Pat. Nos. 4,758,516, 5,023,321, and 4,871,670, Supra).

The methods of the present invention are not restricted to the use of relaxin as hereinabove defined. The use of any compound capable of specific binding to the specific relaxin binding sites in the atrium of the heart and capable of increasing the rate or force of atrial contraction is also contemplated. Receptor binding may be studied by methods known in the art, including the autoradiographic assay disclosed in the examples. Similarly, methods for testing the rate and force of atrial contraction (both in vitro and in vivo) are well known in the art and will be detailed hereinbelow, and specifically disclosed in the examples.

The term "therapeutically effective amount" is used to define an amount resulting in the improvement of a physiological condition to be treated. The actual dose will be different for the various specific physiological conditions and molecules, and will vary with the patient's overall condition, the seriousness of the symptoms, counterindications, etc. The determination of the effective dose is well within the skill of a practicing physician.

Methods for making relaxin A- and B-chains or analog chains are known in the art [see e.g. Barany, G. and Merrifield, R. B. *The Peptides* 2, 1 (1980), Gross E. and Meienhofer, J. (eds.), Academic Press, New York], as are methods for combining the A-and B-chains to provide relaxin (Tregear et al., in *Biology of Relaxin and its Role in the Human*, Bigazzi et al. (eds.), Elsevier N.Y., N.Y. pp. 42-55; Johnston et al., Supra, EP 251,615, published Jan. 7, 1988 and U.S. Pat. No. 4,835,251, issued May 30, 1989). Similarly, there are numerous methods known in the art for isolating and purifying relaxin from various natural sources (see e.g. EP 107,782 and EP 107,045).

The relaxin herein may, for example, be prepared by synthesis of the A and B chains, and purification and assembly thereof, as described in EP 251,615, Supra, and U.S. Pat. No. 4,835,251, Supra or in WO 90/13659 (published Nov. 15, 1990). For synthetic relaxin, a 4:1 molar ratio of A to B chain is generally employed. The resulting product is then purified by any means known to one of ordinary skill in the art, including, reverse-phase HPLC, ion exchange chromatography, gel filtration, dialysis, or the like, or any combination of such processes.

The relaxin amino acid sequence variants are preferably constructed by mutating the DNA sequence that encodes the respective chain(s) of the corresponding native (wild-type) relaxin or a known relaxin derivative. Generally, particular regions or sites of the DNA will be targeted for mutagenesis, and thus the general methodology employed to accomplish this is termed site-directed mutagenesis. The mutations are made using DNA modifying enzymes such as restriction endonucleases (which cleave DNA at particular locations), ligases (which join two pieces of DNA together) nucleases (which degrade DNA) and/or polymerases (which synthesize DNA).

1. Simple Deletions and Insertions

Restriction endonuclease digestion of DNA followed by ligation may be used to generate deletions, as described in section 15.3 of Sambrook et al. (*Molecular Cloning: A Laboratory Manual*, Second Edition, Cold Spring Harbor Laboratory Press, New York [1989]). To use this method, it is preferable that the foreign DNA be inserted into a plasmid vector. A restriction map of both the foreign (inserted) DNA and the vector DNA must be available, or the sequence of the foreign DNA and the vector DNA must be known. The foreign DNA must have unique restriction sites that are not present in the vector. Deletions are then made in the foreign DNA by digesting it between these unique restriction sites, using the appropriate restriction endonucleases under conditions suggested by the manufacturer of the enzymes. If the restriction enzymes used create blunt ends or cohesive ends, the ends can be directly ligated together using a ligase such as bacteriophage T4 DNA ligase and incubating the mixture at 16° C. for 1-4 hours in the presence of ATP and ligase buffer as described in section 1.68 of Sambrook et al., supra. If the ends are not compatible (non-cohesive), they must first be made blunt by using the Klenow fragment of DNA polymerase I or bacteriophage T4 DNA polymerase, both of which require the four deoxyribonucleotide triphosphates to fill-in the overhanging single-stranded ends of the digested DNA. Alternatively, the ends may be blunted using a nuclease such as nuclease S1 or mungbean nuclease, both of which function by cutting back the overhanging single strands of DNA. The DNA is then religated using a ligase. The resulting molecule is a relaxin chain deletion variant.

A similar strategy may be used to construct insertion variants of relaxin chains, as described in section 15.3 of Sambrook et al., supra. After digestion of the target foreign DNA at the unique restriction site(s), an oligonucleotide is ligated into the site where the foreign DNA has been cut. The oligonucleotide is designed to code for the desired amino acids to be inserted and additionally has 5' and 3' ends that are compatible with the ends of the foreign DNA that have been digested, such that direct ligation is possible.

2. Oligonucleotide-Mediated Mutagenesis

Oligonucleotide-directed mutagenesis is the preferred method for preparing substitution variants of the relaxin chains. It may also be used to conveniently prepare deletion and insertion variants. This technique is well known in the art as described by Adelman et al. (DNA, 2:183 [1983]).

Generally, oligonucleotides of at least 25 nucleotides in length are used to insert, delete or substitute two or more nucleotides in the relaxin molecule. An optimal oligonucleotide will have 12 to 15 perfectly matched nucleotides on either side of the nucleotides coding for the mutation. This ensures that the oligonucleotide will hybridize properly to the single-stranded DNA template molecule. The oligonucleotides are readily synthesized using techniques well known in the art such as that described by Crea et al. (*Proc. Nat'l. Acad. Sci. USA*, 75:5765 [1978]).

The DNA template molecule is the single-stranded form of the vector with its wild-type cDNA relaxin chain insert. The single-stranded template can only be generated by those vectors that are either derived from bacteriophage M13 vectors (the commercially available M13mp18 and M13mp19 vectors are suitable), or those vectors that contain a single-stranded phage origin of replication as described by Veira et al. (*Meth. Enzymol.*, 153:3 [1987]). Thus, the cDNA of the relaxin chain that is to be mutated must be inserted into one of these vectors in order to generate single-stranded template. Production of the single-stranded template is described in sections 4.21–4.41 of Sambrook et al., supra.

To mutagenize wild-type relaxin chains, the oligonucleotide is annealed to the single-stranded DNA template molecule under suitable hybridization conditions. A DNA polymerizing enzyme, usually the Klenow fragment of *E. coli* DNA polymerase I, is then added. This enzyme uses the oligonucleotide as a primer to complete the synthesis of the mutation-bearing strand of DNA. Thus, a heteroduplex molecule is formed such that one strand of DNA encodes the wild-type relaxin chain inserted in the vector, and the second strand of DNA encodes the mutated form of the relaxin chain inserted into the same vector. This heteroduplex molecule is then transformed into a suitable host cell, usually a prokaryote such as *E. coli* JM101. After growing the cells, they are plated onto agarose plates and screened using the oligonucleotide primer radiolabeled with 32-P to identify the colonies that contain the mutated chain. These colonies are selected, and the DNA is sequenced to confirm the presence of mutations in the relaxin chain.

Mutants with more than one amino acid substituted may be generated in one of several ways. If the amino acids are located close together in the polypeptide chain, they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant. The first round is as described for the single mutants: wild-type relaxin DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

To express the DNA encoding the relaxin chain variant as a polypeptide, this DNA is excised from the vector and inserted into an expression vector that is appropriate for eukaryotic host cell expression.

The variant relaxin chains can be assembled to yield a functional relaxin molecule by methods known in the art, as detailed hereinabove and illustrated in the Preparation Example.

A B-31 analog of H2 relaxin (deletion of the C-terminal Ser-Leu) was produced by incubation of H2 relaxin with carboxypeptidase A (Cooper Biomedical, 0.2 unit/100 µg relaxin) in 0.2M N-ethylmorpholine, pH 8.2, for 60 minutes at 37° C. Under such conditions, the removal of the two amino acids was complete as judged by HPLC on a Vydac C18 reversed phase column using a gradient of 30–40% acetonitrile in 0.1% TFA. Amino acid analysis and mass spectrometry confirmed the removal of only those two amino acid residues. Other, truncated relaxin derivatives can be made in an analogous manner.

The cardiovascular effects of relaxin and other compounds capable of specific binding to a relaxin receptor in the atrium of the heart, can be studied by standard methods developed for testing known positive inotropic agents. The tests include hemodynamic measurements, including the measurement of heart rate and arterial pressure; blood volume measurements; and hormone assay and sampling procedures, including the measurement of plasma vasopressine and atrial natriuretic factor levels.

General procedures for in vitro evaluation of the effects of relaxin on the atrial muscle are disclosed in Example 3. The effect of other compounds which are capable of specific binding to a relaxin receptor in the atrium of the heart on the force or rate of atrial contraction can be evaluated in an analogous manner.

In vivo cardiovascular measurements in the unanesthetized, freely behaving rat are known in the art [Ward, D. G., et al., *Genentech Reports* No. 88-485-561 (1989)]. According to this procedure, the rats are anesthetized with ketamine hydrochloride (150 mg/kg) in order to cannulate the left iliac artery and to implant an osmotic pump. This technique is detailed in Example 2, along with its application for determining the heart rate and uterine weight.

Further parameters which can be determined in this model include the measurement of blood volume, which is based on the dilution of Evans blue dye (T1824). Prior to the initial determination of blood volume, Evans blue (1 mg/kg, in a volume of 0.5 ml) is injected via the arterial cannula in order to saturate the reticulo-endothelial system. For each subsequent measurement, a blood sample (0.5 ml) is drawn, Evans blue is injected and a second blood sample is drawn after 1.5 minutes. The concentration of Evans blue in plasma is measured spectrophotometrically to determine plasma volume and the blood volume is calculated as plasma volume+(plasma volume×hematocrit)/(1-hematocrit). After each blood sample, the red cells are suspended in sterile saline and reinfused.

Plasma vasopressin and natriuretic factor can be measured by radioimmunoassay. Serum relaxin levels can be determined by an enzyme-linked immunosorbent assay (ELISA). Blood samples (2 ml) are drawn from the arterial cannula and centrifuged for 90 msec at 14,000 rpm. The plasma is mixed with EDTA and frozen immediately; the red cells are suspended in sterile saline and reinfused.

The in vivo cardiovascular effects of relaxin and other compounds specifically binding to the atrial relaxin receptors can also be evaluated in the anesthetized open-chest dog model described by Evans, D. B. et al., in *Drug Devel. Res.* 9, 143-157 (1986). The direct vasodilator activity of relaxin can be tested in the anesthetized dog by examining its effect on forelimb perfusion [Steffen et al., *J. Cardiovasc. Res.* 520-526 (1986)]. The effect of relaxin on blood flow to the heart can, for example, be evaluated in the anesthetized dog, using radiolabeled microspheres [Steffen, R. P. et al., *New Cardiovascular Drugs*, New York, Raven Press, 1986, p.81]. The cardiovascular hemodynamics, such as cardiac output, left ventricular contractility and arterial blood pressure can also be measured in the conscious dog, for example as described by Steffen, R. P. et al., Supra.

For therapeutic use, relaxin is administered in the form of pharmaceutical formulations. Pharmaceutical compositions comprising an effective amount of human relaxin in a buffer of 4-7, preferably 4.5-5.5 are disclosed in co-pending application Ser. No. 07/303,779, filed Jan. 23, 1989 and in PCT Application Publication No. WO 89/07945 (published Sep. 8, 1989). The relaxin pharmaceutical formulations preferably are in liquid, frozen, or gel form, or may be lyophilized and reconstituted, and contain a therapeutically effective amount of human relaxin. A preferred liquid composition herein is human relaxin in a 10 mM citrate buffer at pH 5, with sodium chloride present to a total ionic strength of about 0.15 $\mu$, representing the proper osmolality. The pharmaceutical compositions herein may comprise the mixture of two or more compounds capable of specific binding to a relaxin receptor in the atrium of the heart, and may optionally contain further agents suitable for the treatment of of diminished cardiac output or any physiological conditions associated therewith, such as diuretics, vasodilators and inotropic agents known to decrease blood volume or peripheral resistance or to increase force of cardiac contraction. Alternatively, one or more such additional agents may be administered in the form of separate pharmaceutical formulations, simultaneously with or consecutively to the administration of relaxin or other compounds specifically binding to the cardiac relaxin receptors.

The therapeutically effective amount of human relaxin and other compounds within the scope of the invention herein is selected based on several variables, including the patient (human, non-human mammalian, avian, etc.), the specific condition being treated, the patient's medical history, and the therapeutic route and schedule being utilized. The therapeutic route includes parenteral administration, such as, e.g., subcutaneous, intraperitoneal, intravenous, and intramuscular administration. The average dose for the treatment of congestive heart failure varies depending on numerous indicia known to the ordinarily skilled physician, including the route and scheduling of administration, the seriousness of the patient's condition, the patient's age, the form of the pharmaceutical composition, and such other considerations as would be known to the physician. A typical continuous subcutaneous dose range for the treatment of human patients is about 1.5 $\mu$g to about 0.15 mg/kg of body weight/day.

Further details of the invention will be apparent from the following, non-limiting examples.

EXAMPLE 1

Autoradiographic Localization of Relaxin Binding Sites in Rat Heart Tissue Sections Human Relaxin Synthetic human (H2) relaxin [Johnston et al., in Peptides: *Structure and Function* Deber, C. M. et al. (eds.) 683-686, Pierce Chemical Company, Rockford, Ill. (1985)], also referred to as "relaxin" in this example, was supplied by E. Rinderknecht (Genentech).

Relaxin was biologically active in the mouse pubic symphysis assay [Steinetz et al., *Endocrinology* 67, 102-115 (1960)] and a cAMP bioassay to be described below. The concentration of relaxin was determined by amino acid analysis.

Phosphorylation of Relaxin Phosphorylation of H2 relaxin with the catalytic subunit of cAMP-dependent protein kinase (from bovine heart muscle, Sigma) and [$\gamma$-$^{32}$P]ATP (specific activity 5000 Ci/mmol, Amersham, Arlington Heights, Ill.) was carried out according to the procedure for the phosphorylation of human IFN-$\gamma$ [Kung, H. F. and Bekesi, E., *Methods Enzymol.* 119, 296-301 (1986)] with modifications. The phosphorylation reaction product was analyzed by instant thin layer chromatography (ITLC, Gelman) which employed glass fiber sheets impregnated with silica. After developing with solvent containing 0.2M KCl, 5% TCA, the TCA-precipitated protein remained at the origin while free ATP migrated to the solvent front as revealed by autoradiography of the chromatogram using Kodak XAR film. After autoradiography, regions containing radioactivity were excised and counted with Aquasol-2 (New England Nuclear) in a Beckman LS 3801 liquid scintillation spectrometer at a counting efficiency of 95% for $^{32}$P. Using this technique the final phosphorylation reaction conditions were determined as follows: human relaxin, 5 $\mu$g, was incubated at 37° C. for 60 min in a reaction mixture (total volume 30 $\mu$l) containing 20mM Tris-HCl, pH 7.5, 100 mM NaCl, 20 mM MgCl$_2$, 25 $\mu$Ci [$\gamma$-$^{32}$P]ATP (167 nM, specific activity 5000 Ci/mmol, Amersham, for the preparation of $^{32}$P-relaxin) or 1.4 mM ATP (Sigma, for preparation of unlabeled phosphorylated relaxin), and 10 units of the catalytic subunit of cAMP-dependent protein kinase from bovine heart muscle (Sigma). At the end of the incubation period the reaction was stopped by placing the mixture on ice and the mixture was subsequently loaded on a Sep-Pak C18 column (Waters) equilibrated with 0.1% TFA, 1 mM ATP. The column was washed first with equilibration buffer and then with 10% acetonitrile in 0.1% TFA. Native relaxin and phosphorylated relaxin were then eluted with 80% acetonitrile in 0.1% TFA, and fractions were analyzed for radioactivity by liquid scintillation counting as described above.

Purification of Phosphorylated Relaxin on Cation Exchange HPLC—HPLC (Poly CAT A, Poly LC, Columbia, Md.) of phosphorylated relaxin was performed using an LKB system. Sep-Pak C18 column eluates containing radioactivity (or equivalent fractions containing unlabeled phosphorylated relaxin) were pooled and injected onto a Poly CAT A column (Poly LC) equilibrated with 50 mM $NaH_2PO_4$, pH 7, 25% acetonitrile (v/v) (buffer A). The column was eluted with a linear gradient of 0–0.5M NaCl in buffer A over 50 min at 1 ml/min. One-min fractions were collected and aliquots were counted for radioactivity as described above. To the peak radioactive fraction was added 1 mg/ml BSA (crystallized, Miles), 1 mM PMSF (Boehringer-Mannheim) and 1 µg/ml leupeptin (Boehringer-Mannheim) and it was stored at 4° C.

Bioassay and ELISA of Phosphorylated Relaxin—The phosphorylated relaxin was assayed for its ability to increase cAMP levels in a primary human uterine cell line. The procedure of Kramer et al. [Kramer et al., In Vitro Cell, Dev, Biol. 26, 647–656 (1990)] Was modified and carried out as follows: human uterine cells at passage 15–22 were grown to confluency in Ham's F12/DMEM (1/1, v/v medium supplemented with 10% heat-inactivated newborn calf serum, 100 unites/ml penicillin, 100 µg/ml streptomycin, 2 mM glutamine and 24 mM HEPES, pH 7.4. Cells were plated into 6-well culture plates at $10^5$ cells/well and incubated overnight at 37° C. and 5% $CO_2$ in air. The cells (at 60–80% confluency) were then washed twice with F12/DMEM-24 mM HEPES, pH 7.4 (buffer B) at room temp. Phosphorylated relaxin samples and standard relaxin solutions (diluted in buffer B with 0.1% BSA and 0.01% Tween-80), along with forskolin (1 µM) and IBMX (0.05 mM) were then added to the cells and incubated at room temperature for 30 min with 0.1N HCl. Aliquots of the extracts were then neutralized with 0.1N NaOH and cAMP levels were measured in a radioimmunoassay. The assay was based on the competition between cAMP and a fixed quantity of $^{125}I$-labeled cAMP (Du Pont) for binding to a goat anti-cAMP antibody (Cambridge). Following incubation at 4° C. for 24 hr the antigen-antibody complex was precipitated with donkey anti-goat IgG (Pelfreeze) in polyethylene glycol at room temperature for 1 hr, and separated by centrifugation and decantation. The radioactivity in the pellet was measured in a gamma counter, and the amount of cAMP in the samples was determined by comparison with a standard cAMP curve. A relaxin standard curve was constructed in which the cAMP concentrations (pmol/ml) determined in the radioimmunoassay were plotted as a function of stimulating relaxin concentrations (ng/ml). The data were fit to a four-parameter equation.

The phosphorylated relaxin was also quantified using a double-antibody ELISA for relaxin [Lucas et al., J. Endocrinol. 120 (1989)]. The assay employed two relaxin affinity-purified antibodies, a goat anti-relaxin antibody coat and a rabbit anti-relaxin horseradish peroxidase conjugated secondary antibody.

Binding of $^{32}P$-Relaxin to Rat Uterus and Heart Tissue Sections Ten-week-old normal male and cyclic female Sprague-Dawley rats (Charles River Breeding Laboratories, Wilmonton, Mass.) were used for binding specificity and binding displacement experiments. These were given food and water ad libidium and housed in a room with the ambient temperature controlled around 21° C.

For hormonal control experiments, 10–11-week-old female rats were ovariectomized for two weeks and then injected s.c. with 10 µg estradiol cyclopentyl propionate in a 0.2% peanut oil vehicle or with vehicle alone. Likewise, 10–11-week-old male rats were castrated for 2 weeks and were injected with either 10 µg estradiol cyclopentyl propionate, 10 µg testosterone, or vehicle alone. The rats were sacrificed 7 days later by asphyxiation with $CO_2$. The relevant tissues were removed rapidly and frozen in powdered dry ice immediately.

The frozen tissues were sectioned to 16 µm thickness using a Reichert-Jung Model 2800 Frigocut cryostat (Cambridge Instruments). Tissue sections were fixed onto gelatin/chromium potassium sulfate treated microscope slides by warming, and immediately refrozen and stored at −80° C. overnight or longer.

For binding of $^{32}P$-relaxin to the tissue sections, frozen slides were prewashed with binding buffer (Hank's balanced salt solution supplemented with 20 mM HEPES, pH 7.2, 1 mg/ml BSA, 0.1 mM PMSF, and 1 µg/ml leupeptin) at 4° C. for 1.5-2 hours. The tissue sections were then covered with 600–700 µl of 100 pM $^{32}P$-relaxin with or without excess unlabeled relaxin and other competing agents as specificity control, and incubated at 4° C. for one hour. The slides were washed 3 times for 15–30 minutes each, with binding buffer. The slides were air-dried and mounted on filter paper and exposed to Hyperfilm-$\beta_{Max}$ (Amersham) for 3–5 days.

Regions of binding were determined by overlaying the autoradiographs with adjacent sections counterstained with hematoxylin-eosin. For relaxin binding displacement experiments, consecutive 16 µm sections were incubated with 100 pM of $^{32}P$-relaxin in the absence and presence of increasing concentrations (serial three-fold increases) of unlabeled relaxin in the range of 0.1–100 nM. Pseudocolor reconstruction and quantitative analysis of $^{32}P$-relaxin binding autoradiographs were performed with a RAS-3000 image analysis system (Amersham). The OD or radioactivities (cpm) of bound $^{32}P$ relaxin (maximum binding in a particular region) were quantified by computerized densitometry based on parallel sets of $^{32}P$-relaxin standards (ranging from 50 to 2000 cpm) blotted onto nitrocellulse membranes (Trans-Blot SF, Bio-Rad, Richmond, Calif.). The binding inhibition data were fit to a four paramter equation to obtain the $ED_{50}$ (the concentration of unlabeled relaxin yielding 50% displacement of the binding of $^{32}P$-relaxin). The dissociation constant ($K_d$) for relaxin was calculated by the method of Cheng and Prusoff [Biochem. Pharmacol. 22, 3099–3108 (1973)].

RESULTS

Relaxin Binding Sites in the Rat Heart-Nine different rat tissues, including the liver, spleen, thymus, kidney, adrenal gland, heart, lung, skin, and testis, were examined in the present studies for the binding of $^{32}P$-relaxin. Of all these tissues the only one which showed binding was the (normal female) rat heart (FIG. 1A). The binding was seen in the atria but not the ventricles. The specificity of binding was demonstrated by the displacement of the binding of 100 pM $^{32}P$-relaxin by 100 nM unlabeled relaxin (FIG. 1B) but not by 100 nM IGF-I (Genentech, Inc.) (FIG. 1C), insulin (Eli Lilly, Pearl River, N.Y.), angiotension II, and atrial natriuretic peptide (Sigma, St. Louis, Mo.) (data not shown). Similar binding in the atria of normal male rat heart (FIG. 1D)

can also be fully displaced by 100 nM unlabeled relaxin (data not shown).

Figure 2B:
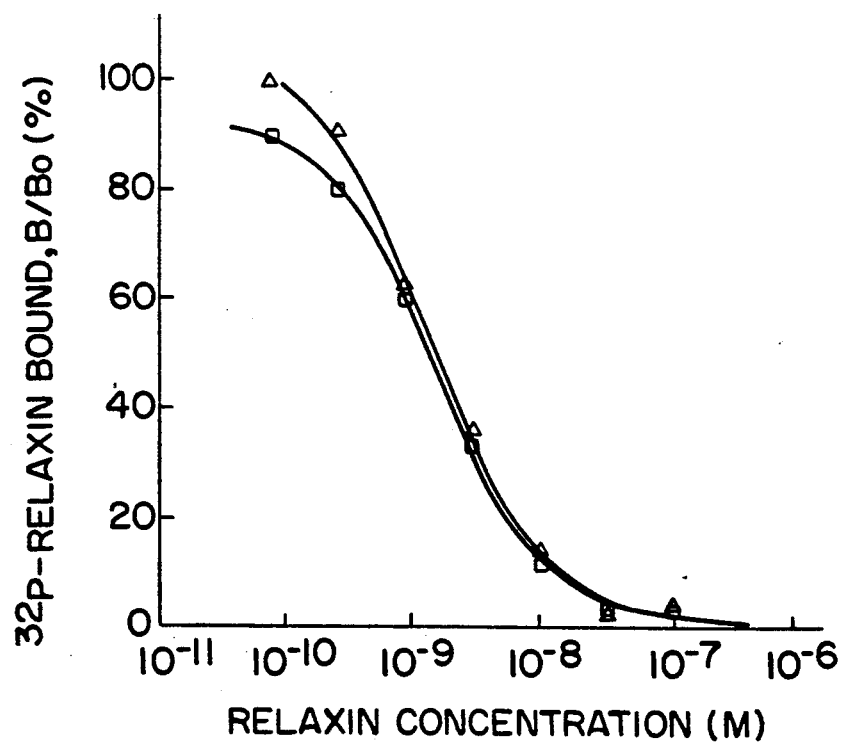

Affinity of Relaxin Binding to Rat Heart and Rat Uterus—Measurements of the inhibition of $^{32}$P-relaxin binding in the presence of increasing concentrations of unlabeled relaxin yield a displacement curve consistent with a single class of relaxin binding sites in the rat uterus (FIG. 2A) and heart (FIG. 2B and 2C). While total displacement was achieved in the heart (FIG. 2B and 2C), partial displacement was observed in the uterus (FIG. 2A). The dissociation constant ($K_d$) for relaxin was calculated as the mean±S.E. of two separate regions on the same tissue: 1.3±0.22 nM in the uterus (FIG. 2A), and 1.37±0.13 nM in the normal heart (FIG. 2B), and 0.86±0.35 nM in the estrogen-treated ovariectomized rat heart (FIG. 2C).

Analogous displacement curve was obtained with H1 relaxin in the atrium of female rat heart (FIG. 3). The dissociation constant ($K_d$) for H1 relaxin was found to be 1.53±0.04 nM.

Figure 4A:
FIG. 4 shows the binding of 100, pM $^{32}$P-relaxin in the atria of A. ovariectomized female rat; B. ovariectomized female rat treated with estrogen; C. normal cycling female rat; and D. normal female treated with estrogen. The enhanced color spectrum is shown in D. E. is a portion of an hematoxylin-eosin stained female rat heart section which corresponds to the region marked by ←→ in C. Original magnification: 10 x.
Figure 4C:
Figure 4B:
Figure 4D:
Figure 4E:

Effect of Steroid Hormones on Relaxin Receptors in the Rat Heart. Ovariectomy did not change the $^{32}$P-relaxin binding in the female rat heart (FIGS. 4A and B). Likewise, castrated male rat hearts showed the same relaxin binding as intact male rat hearts (data not shown). Estrogen treatment of normal or ovariectomized female rats had no effect on relaxin binding in the heart (FIGS. 4C and 4D). Likewise, testosterone treatment of intact or castrated male rats, or estrogen-primed castrated male rats, did not cause any changes in relaxin binding in the heart (data not shown). The above data were repeated in a separate set of experiments using different tissue sections. The affinity of relaxin binding to the atria in estrogen-treated ovariectomized rats ($K_d$=0.86±0.35 nM, FIG. 2C) is not significantly different from that in intact female atria (1.37±0.13 nM, FIG. 2B).

Earlier reports on the specific binding of a $^{32}$P-labeled H2 relaxin to the rat uterus and brain [Osheroff, P. L., et al., *J. Biol. Chem.* 265, 9396-9401 (1990); and *Proc. Natl. Acad. Sci. USA*, 88, 6413-6417 (1991)] suggested that, in addition to its roles in pregnancy, relaxin might have other physiological roles as well.

In this study the binding of relaxin to various other rat tissues was examined, and it was surprisingly found that the heart was the only tissue among these which showed relaxin binding. The binding was localized in particular to the atria, but not the ventricles. The very selective tissue distribution of relaxin receptors in general is intriguing and may be indicative of certain novel functions relaxin may have in these tissues. The specific binding to the atrium suggests that relaxin may be involved in the control of atrial functions.

The source of relaxin for the atrial binding sites in unknown at present. Although the highest circulating levels of relaxin are found during pregnancy, detectable levels (30-150 pg/ml) have been reported in the peripheral blood during the non conceptive luteal phase [Stewart, D. R., et al., *J. Clin. Endocrinol. Metab.* 70, 1771-1773 (1990)]. Circulating levels of relaxin have not been established in the male. However, immunoreactive and biologically active relaxin has been reported in human seminal plasma (average 45 ng/ml) and the likely source was the prostate [Loumaye, E. et al., *J. Clin. Endocrinol. Metab.* 50, 1142-1143 (1980); Essig, M., et al., *Ann. N.Y. Acad. Sci.* 380, 224-230 (1982); Weiss, G., Biol. Reprod. 40, 197-220 (1989)]. The possible synthesis of relaxin in the heart also cannot be ruled out. In situ hybridization experiments will provide the answers to this latter possibility.

The specificity and affinity of relaxin binding in the atriuum, the uterus, and brain are similar to one another. The observation of a significant decrease in uterine relaxin receptors following overiectomy seems to suggest that uterine relaxin receptors are estrogen dependent. A different picture exists in the heart. The affinity of relaxin binding in the male atrium is indistinguishable from that in the female atrium, similar to the condition seen in the male and female brain. Furthermore, the concentrations of relaxin receptors are independent on sex steroids.

EXAMPLE 2

The Effect of Continuous Subcutaneous Infusion of H2 Relaxin on the Heart Rate of Female Rats Groups (4 to 9 animals in each group) of conscious, non-pregnant, Spontaneously Hypertensive (SHR) and Sprague-Dawley (SD) female rats weighing about 144-385 g each, were used in this experiment. The rats were anesthetized with ketamine hydrochloride (150 mg/kg) in order to cannulate the left iliac artery and to implant an osmotic pump. All surgery was performed under aseptic conditions. Streched PE 50 tubing was fitted with an injection cap and flushed with heparinized saline, routed subcutaneously, exteriorized between the capsulae, and passed through a spring tether that is anchored to the skin with a nylon button. Extreme care was taken in cannulating the left iliac artery to avoid damage to collateral circulation and local innervation. An (Alzet) osmotic pump filled with relaxin or vehicle was then inserted into a subcutaneous pocket caudal to the exit point of the cannula.

All wounds were closed with suture, infiltrated with Xylocaine and coated with Betadine. The animals were returned to their cages where the cannulae were connected to freely rotating sqivels to permit unobstructed movement. Arterial pressure, heart rate, water intake, urine volume and vascular blood volume were measured daily throughout the duration of the experiments.

Arterial pressure and heart rate were measured directly through the arterial cannulae with standard pressure transducers (Stoelting) and strain gauge amplifiers (Stoelting). Arterial pressure was sampled (30/sec) with an A/D converter (Metrabyte DAS-8) for online display and storage on magnetic disks (Tandy 1000 computer). Mean arterial pressure and heart rate for specific intervals of time were integrated and averaged from these stored data.

Figure 5:
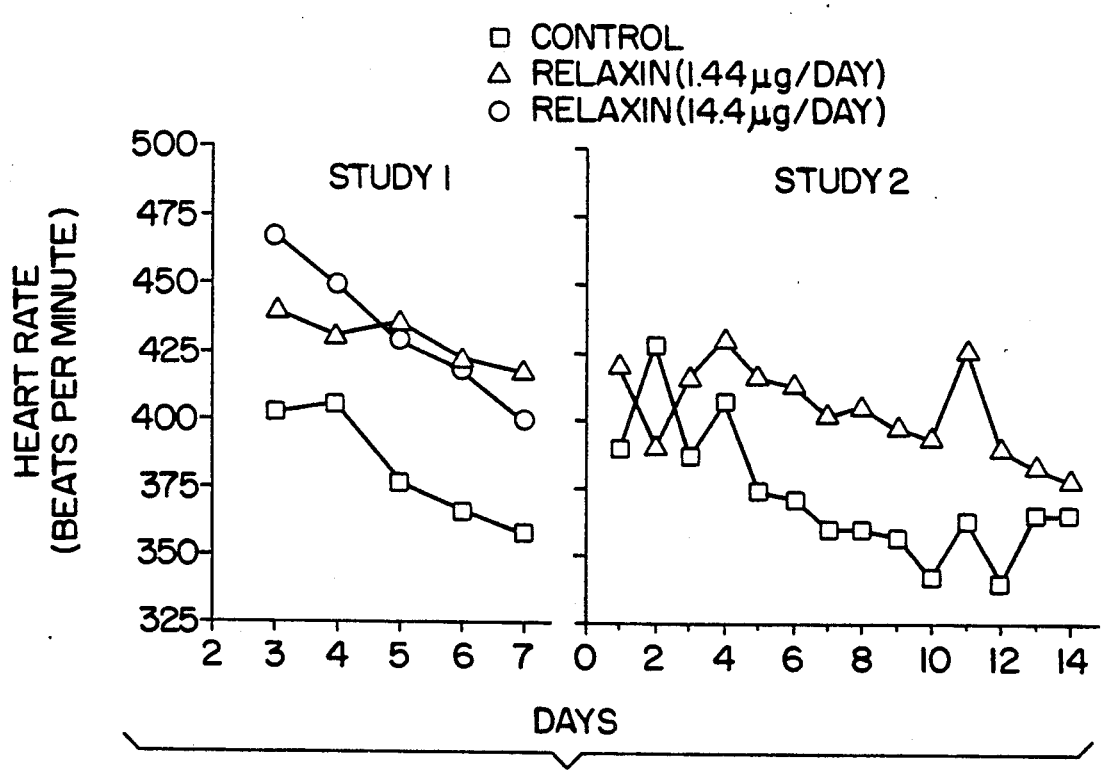
FIG. 5 shows the effect of continuous subcutaneous infusion of H2 relaxin on the heart rate of spontaneously hypertensive (SHR) female rats.
Figure 6:
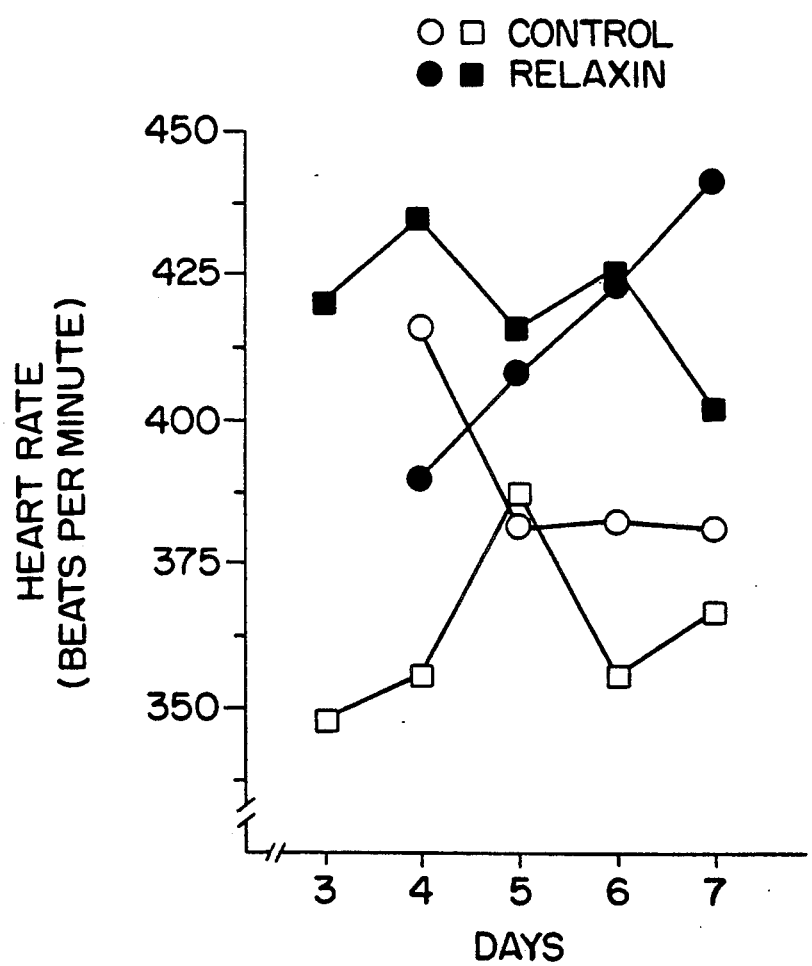
FIG. 6 shows the effect of continuous subcutaneous infusion of H2 relaxin on heart rate in normotensive, non-pregnant female Sprague Dawley (SD) rats.
Figure 7:
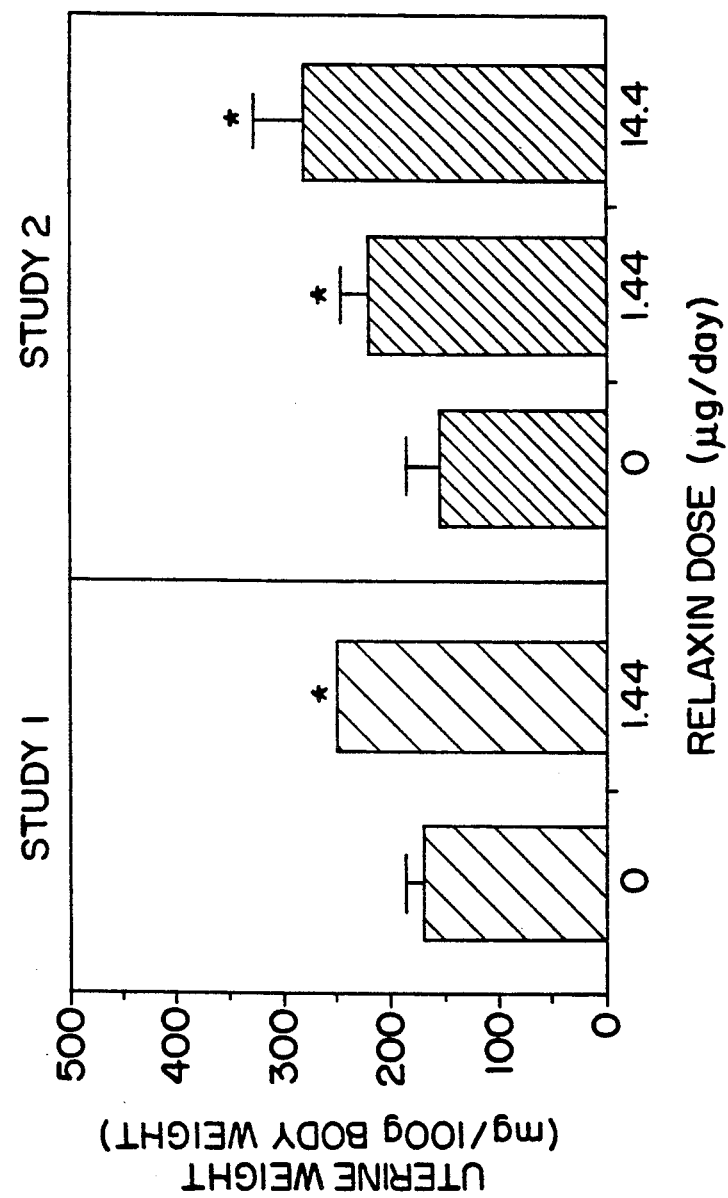
FIG. 7 shows the increase of uterine weight in response to continuous subcutaneous infusion of H2 relaxin in the same spontaneously hypertensive (SHR) rats as FIG. 5.
Figure 8:
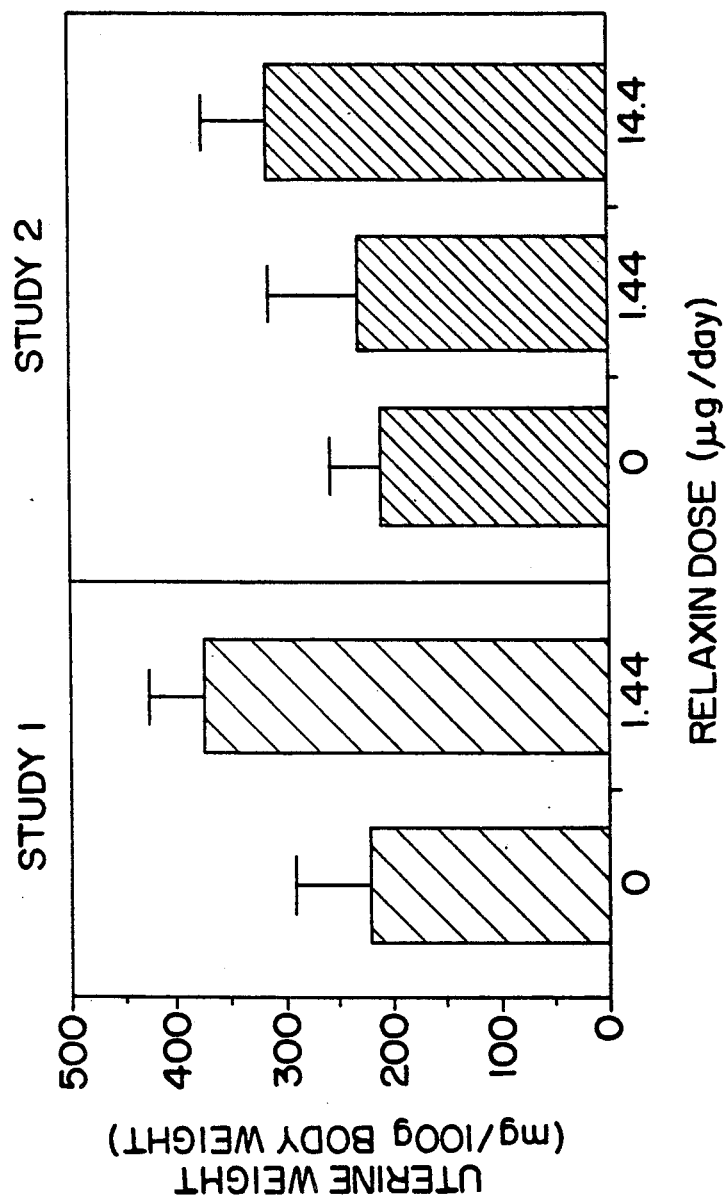
FIG. 8 shows the increase of uterine weight in response to continuous subsutaneous infusion of H2 relaxin in the same normotensive, non-pregnant female Sprague Dawley (SD) rats as FIG. 6.

H2 relaxin was infused continuously and subcutaneously with an Alzet osmotic pump at a rate of either 1 or 10 ng/min. The effect on heart rate in SHR and SD rats, respectively, is illustrated in FIGS. 5 and 6. The results shown in FIG. 6 were obtained with a dose of 1.44 μg/day for Study #1, and μg/day for Study #2. Complete uteri were dissected after euthanasia, and weighed to the nearest mg wet weight. As shown in FIGS. 7 and 8 (SHR and SD rats, respectively), the bioactivity of H2 relaxin was confirmed by increased uterine weights.

EXAMPLE 3

Effect of H2 Relaxin on Atrial Contraction and Atrial Rate

The cardiac atria contain stretch receptors that signal the brain concerning atrial filling, contraction and tension. The observations that relaxin receptors are located in the cardiac atria (Example 1) and in selected autonomic nuclei of the hypothalamus (Osheroff, et al., Supra) suggest that relaxin may play a critical role in modifying the responses of atrial stretch receptors. The direct effect of relaxin on the atrial muscle was evaluated in the following in vitro experiments.

Materials—Krebs-Henseleit solution was prepared with the following composition (in millimoles): NaCl 118; KCl 4.7; $MgSO_4$ 1.64; $NaHCO_3$ 24.88; $KH_2PO_4$ 1.18; d-glucose 11.1; bubbled with 95% $O_2$/5% $CO_2$; $CaCl_2$ 2.52.

Human (H2) relaxin (hRLx-2, 1.5 mg/ml; Genentech) was diluted fresh daily to desired concentrations (500:1; 5000:1; 50000:1) in Krebs-Henseleit solution.

Tissue Harvest—Male Wistar rats (Charles River) weighing 475–525 g each, were anesthetized with sodium pentobarbital (60 mg/kg). After thoracotomy, the heart was removed rapidly and placed in cold (4° C.) Krebs-Henseleit solution until spontaneous contractions ceased. The right and left atria were excised.

Experimental Apparatus—Tissue was bathed in an organ chamber holding 42 ml Krebs-Henseleit solution that was aerated with 95% $O_2$/5% $CO_2$ and heated to 37° C. with a temperature controlled water jacket. Tissue contractions were measured with force-displacement transducers (Grass FT 0.3) and recorded on chart paper (Grass moled 79 polygraph). The rates of contrations were determined with a cardiotachometer (Grass). Electrical stimulation of tissue was induced through bipolar clip electrodes connected to a stimulator through a stimulus isolation unit (Grass model S48).

Measurement of Right Atrial Rate—Stainless steel clips weighing 0.5 g each were attached to each end of the right atrium. One clip was secured to a hook within the organ chamber and the other clip was attached to the force-displacement transducer. The position of the transducer was adjusted to yield 0.5 g resting tension.

Measurement of Left Atrial Contraction—A stainless steel clip was attached to the distal end of the left atrium and the proximal end was attached to a bipolar electrode. The electrode assembly was secured within the organ chamber and the upper clip was attached to the force-displacement transducer. The position of the transducer was adjusted to yield 1.0 g resting tension. The left atrium was stimulated at 3 Hz at 1.5x threshold. The duration (3 msec) and intensity of the pulses (1.5–3.0 Volts) were kept constant throughout an experiment.

Dose-Response Curve—In all experiments the atria were allowed to stabilize for 30 minutes prior to addition of drugs. Preliminary experiments indicated that relaxin was not readily washed off of the atrial tissues. Thus, cumulative dose-response curves were generated. At 10 minute intervals, relaxin was added to each organ chamber to obtain bath concentrations of 100 pg/ml, 300 pg/ml, 1 ng/ml, 3 ng/ml, 10 ng/ml and 30 ng/ml.

Analysis of Data—Measurement of contraction rate and force of contraction following each dose of relaxin were obtained after responses reached a steady state. Rate was determined directly from the output of the cardiotachometer. Force of contraction was measured as the magnitude of the contractile twitches. In order to adjust for variations between tissues, data are expressed as percent changes from pre-drug values, as means±standard errors. Measurements of rate were obtained in seven right atria; measurement of contractile force were obtained in four left atria.

RESULTS

The readings of the right atrial heart rate measurement are shown in the following Table 1.

TABLE 1

| Dose/Exp. # | 0 | 30 pg | 100 pg | 300 pg | 1 ng | 3 ng | 10 ng | 30 ng |
|---|---|---|---|---|---|---|---|---|
| 1 | 245 | | | | | | 345 | |
| 2 | 290 | | 290 | 300 | 320 | 345 | 390 | 400 |
| 3 | 270 | | 270 | 295 | 310 | 350 | 390 | |
| 4 | 290 | | 290 | 300 | 350 | 400 | 445 | 450 |
| 5 | 300 | | 300 | 310 | 320 | 360 | 370 | 385 |
| 6 | 015 | | 320 | 330 | 345 | 365 | 385 | 395 |
| 7 | 300 | | 300 | 300 | 320 | 350 | 380 | 405 |
| Exp. # | % Δ | | | | | | | |
| 1 | 0 | | | | | | 41 | |
| 2 | 0 | | 0 | 3 | 10 | 19 | 34 | 38 |
| 3 | 0 | | 0 | 9 | 15 | 30 | 44 | |
| 4 | 0 | | 0 | 3 | 21 | 38 | 53 | 55 |
| 5 | 0 | | 0 | 3 | 7 | 20 | 23 | 28 |
| 6 | 0 | | 1 | 5 | 10 | 16 | 22 | 25 |
| 7 | 0 | | 0 | 0 | 7 | 17 | 27 | 35 |
| X | 0 | 0.17 | 3.83 | 11.67 | 23.33 | 32.0 | 36.2 | |
| SD | | ±0.32 | 2.73 | 4.95 | 7.99 | 15.47 | 10.50 | |
| SEM | | 0.14 | 1.22 | 2.21 | 3.57 | 6.32 | 5.25 | |

Figure 9:
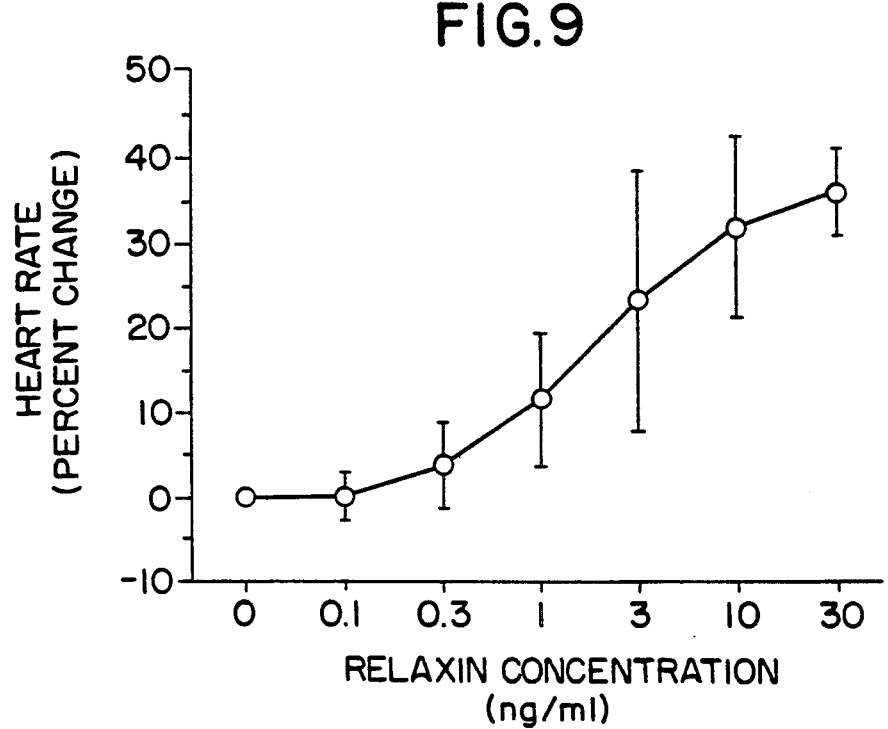
FIG. 9 shows the dose dependent increase in the heart rate of the right atria of male rats in response to in vitro relaxin treatment.

The average spontaneous contraction rate of the right atrium prior to dosing was 287±9.4 beats/min. As shown in FIG. 9, relaxin led to a dose dependent increase in contraction rate that averaged 36% with the 30 ng/minute dose. The point of half maximal increase in contraction rate occurred at about 1.8 ng/ml.

The results of the contractility measurements on electrically spaced left atrium are summarized in Table 2.

TABLE 2

| Dose/Exp. # | 0 | 30 pg | 100 pg | 300 pg | 1 ng | 3 ng | 10 ng | 30 ng |
|---|---|---|---|---|---|---|---|---|
| 5 | 0.68 gm | — | 0.60 | 0.55 | 0.65 | 0.75 | 0.83 | 0.35 gm |
| 6 | 1.05 | — | 1.00 | 0.95 | 1.10 | 1.30 | 1.45 | 1.50 |
| 7. | 0.50 | | 0.48 | 0.45 | 0.48 | 0.58 | 0.70 | 0.78 |
| 8 | 0.75 | | 0.73 | 0.75 | 0.80 | 0.80 | 0.90 | 0.95 |
| Exp. # | % Δ | | | | | | | |

TABLE 2-continued

|     | 30 pg | 100 pg | 300 pg | 1 ng | 3 ng | 10 ng | 30 ng |
|-----|-------|--------|--------|------|------|-------|-------|
| 5   | 0     | −12    | −19    | −14  | 10   | 22    | 25    |
| 6   | 0     | −5     | −9     | 5    | 24   | 38    | 43    |
| 7   | 0     | −4     | −10    | −4   | 16   | 40    | 56    |
| 8   | 0     | −3     | 0      | 7    | 7    | 20    | 27    |
| X   |       | −6     | −9.5   | 1.0  | 14.3 | 30    | 37.8  |
| SD  |       | 3.53   | 6.73   | 5.05 | 6.50 | 9.06  | 12.6  |
| SEM |       | 2.04   | 3.88   | 2.92 | 3.75 | 5.23  | 7.30  |

Figure 10:
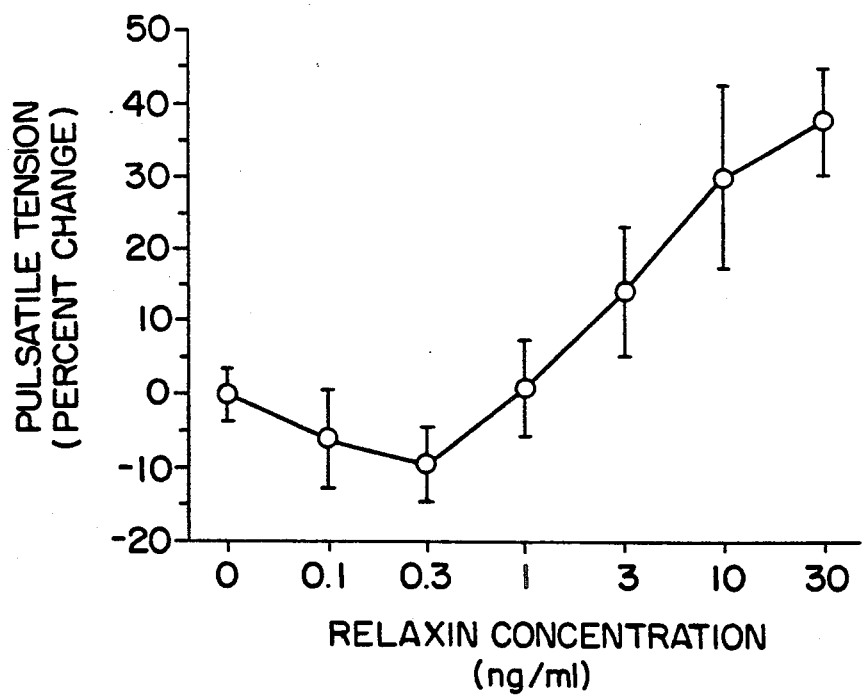
FIG. 10 shows the responses of electrically paced left atria of male rats to in vitro relaxin treatment.

The average magnitude of the contractile twitches of the electrically paced left atrium was 0.75±0.11 g. As shown in FIG. 10, relaxin led to a biphasic dose effect on contractile force. A peak decrease in contractile force of 10% occurred at 300 pg/ml, whereas a peak increase of 38% occurred at 30 ng/ml. The point of half maximal increase in contractile force occurred at about 4.8 ng/ml.

In earlier experiments we have found that intravenous injection of relaxin is associated with a small but consistent increase in heart rate and decrease in systolic and diastolic pressure.

These results are strikingly similar to the dose-related increase of myocardial contractility in response to other inotropic drugs, which has been reported to be accompanied by a dose-dependent decrease in blood pressure and with a minimal increase in heart rate [Evans, D. B. et al., *Pharmacologist* 25, 550 (1983); Evans, D. B. et al., *Drug Devel Res.* 9, 143–157 (1986); and Weishaar, R. E. et al., *Cardiovascular Drugs and Therapy* 3, 29–42 (1989)].

All citations cited throughout the specification, and the reverences cited therein, are hereby expressly incorporated by reference.

Although the foregoing refers to particular preferred embodiments, it will be understood that the present invention is not so limited. It will occur to those ordinarily skilled in the art that various modifications may be made to the disclosed embodiments without diverting from the overall concept of the invention. All such modifications are intended to be within the scope of the present invention.

We claim:

1. A method for increasing cardiac output by administering to a patient exhibiting pathologically diminished cardiac output a therapeutically effective amount of a compound capable of specific binding to a relaxin receptor in the atrium of the heart and increasing the force or rate of atrial contraction.

2. The method of claim 1 wherein said compound is relaxin.

3. The method of claim 2 wherein said patient is human and said compound is a human relaxin.

4. The method of claim 3 wherein said compound is an H2 relaxin or an H1 relaxin.

5. The method of claim 4 wherein said compound comprises the amino acid sequence of native H2 relaxin or H1 relaxin.

6. The method of claim 4 wherein said compound comprises a full-length A-chain and a carboxy-terminal shortened B-chain of H2 relaxin or H1 relaxin.

7. The method of claim 4 wherein said compound comprises a combination of any one of H2 relaxin A-chains A(1-24), A(2-24), A(3-24) with any one of H2 relaxin B-chains B(-1-23) to B(-1-32).

8. The method of claim 4 wherein H2 relaxin or H1 relaxin is administered in the form of a liquid, injectable pharmaceutical formulation.

9. The method of claim 8 wherein said formulation comprises a therapeutically effective amount of H2 relaxin in a buffer of 4.5 to 5.5.

10. A method of treating heart failure by administering to a patient in need of such treatment a therapeutically effective amount of a compound capable of specific binding to a relaxin receptor in the atrium of the heart and increasing the force or rate of atrial contraction.

11. The method of claim 10 wherein the heart failure is congestive heart failure.

12. The method of claim 11 wherein said patient is human and said compound is relaxin.

13. The method of claim 12 wherein said compound is an H2 relaxin or an H1 relaxin.

14. The method of claim 13 comprising the administration of a further therapeutic agent suitable for the treatment of heart failure or a condition associated therewith.

15. The method of claim 13 wherein said heart failure is acute heart failure and said administration is by intravenous injection of a liquid pharmaceutical formulation comprising a therapeutically effective amount of H2 relaxin or H1 relaxin.

16. A method of stimulating cardiac inotropy and chronotropy, comprising administering to a patient in need of such stimulation a therapeutically effective amount of a compound capable of specific binding to a relaxin receptor in the atrium of the heart and increasing the force or rate of atrial contraction.

17. The method of claim 16 wherein said compound is relaxin.

18. The method of claim 16 wherein said compound is an H2 relaxin or an H1 relaxin.

19. The method of claim 18 comprising the administration of a further therapeutic agent capable of stimulating cardiac inotropy.

20. A method of restoring cardiac function following acute heart failure comprising intravenously administering to a patient in need of such treatment a liquid pharmaceutical formulation comprising a compound capable of specific binding to a relaxin receptor in the atrium of the heart, in an amount capable of restoring myocardial contractility to a predepression level.

21. The method of claim 20 wherein said compound is relaxin.

22. The method of claim 21 wherein said compound is an H2 relaxin or an H1 relaxin.

23. The method of claim 22 further comprising treatment with at least one further cardiovascular agent.

* * * * *